United States Patent
Kuhn et al.

(10) Patent No.: US 7,997,899 B2
(45) Date of Patent: Aug. 16, 2011

(54) DENTAL, DENTAL-MEDICAL OR DENTAL-TECHNICAL HANDPIECE WITH ELECTRIC MOTOR

(75) Inventors: Bernhard Kuhn, Biberach (DE); Bernd Gugel, Ulm-Einsingen (DE)

(73) Assignee: Kaltenbach & Voigt GmbH, Biberach (DE)

( * ) Notice: Subject to any disclaimer, the term of this patent is extended or adjusted under 35 U.S.C. 154(b) by 239 days.

(21) Appl. No.: 12/159,067

(22) PCT Filed: Mar. 7, 2007

(86) PCT No.: PCT/EP2007/001967
§ 371 (c)(1),
(2), (4) Date: Aug. 15, 2008

(87) PCT Pub. No.: WO2007/101680
PCT Pub. Date: Sep. 13, 2007

(65) Prior Publication Data
US 2009/0004622 A1 Jan. 1, 2009

(30) Foreign Application Priority Data

Mar. 9, 2006 (DE) .......................... 10 2006 010 976
Oct. 31, 2006 (DE) .......................... 10 2006 051 510

(51) Int. Cl.
*A61C 1/00* (2006.01)
(52) U.S. Cl. ...................................................... 433/131
(58) Field of Classification Search .................. 433/131, 433/103, 114
See application file for complete search history.

(56) References Cited

U.S. PATENT DOCUMENTS

| 4,212,640 | A | * | 7/1980 | Loge et al. ...................... 433/82 |
| 4,235,595 | A | * | 11/1980 | Arnegger ...................... 433/131 |
| 4,251,212 | A | | 2/1981 | Worschischek et al. |
| 4,278,907 | A | | 7/1981 | Landgraf et al. |
| 4,486,176 | A | * | 12/1984 | Tardieu et al. ................. 433/133 |
| 4,518,355 | A | | 5/1985 | Hoffmeister et al. |
| 5,554,896 | A | * | 9/1996 | Hogan .......................... 307/150 |
| 5,689,159 | A | * | 11/1997 | Culp et al. ................. 318/400.18 |

(Continued)

FOREIGN PATENT DOCUMENTS

| DE | 28 34 099 | 2/1980 |
| DE | 93 15 428 | 1/1994 |
| DE | 43 29 181 | 3/1994 |
| DE | 101 35 155 | 5/2002 |

(Continued)

OTHER PUBLICATIONS

International Search Report for PCT/EP2007/001967 dated Aug. 23, 2007.

*Primary Examiner* — John J Wilson
(74) *Attorney, Agent, or Firm* — Marshall, Gerstein & Borun LLP

(57) ABSTRACT

In a dental, dental-medical or dental-technical handpiece, having an elongate grip sleeve there are provided at the rearward end of the grip sleeve coupling elements for the connection of the handpiece to a supply hose to be connected with a dental supply arrangement, and there are provided at the forward end of the grip sleeve a head section with a tool receiver for mounting a tool to be put into rotation. The handpiece further has an electric motor for driving a tool held by the tool receiver, which motor is completely integrated into the grip sleeve such that grip sleeve and motor form a unit.

15 Claims, 5 Drawing Sheets

U.S. PATENT DOCUMENTS

| | | | |
|---|---|---|---|
| 5,846,078 A * | 12/1998 | Rosenstatter | 433/132 |
| 6,042,377 A * | 3/2000 | Ito | 433/126 |
| 6,132,213 A | 10/2000 | Knorpp et al. | |
| 6,899,538 B2 | 5/2005 | Matoba et al. | |
| 2005/0116578 A1 * | 6/2005 | Fleury et al. | 310/254 |

FOREIGN PATENT DOCUMENTS

| | | |
|---|---|---|
| EP | 0 012 871 | 7/1980 |
| EP | 0 888 091 | 1/1999 |
| GB | 2 118 838 | 11/1983 |
| GB | 2 371 488 | 7/2002 |

* cited by examiner

US 7,997,899 B2

DENTAL, DENTAL-MEDICAL OR DENTAL-TECHNICAL HANDPIECE WITH ELECTRIC MOTOR

BACKGROUND TO THE INVENTION

1. Field of the Invention

The present invention relates to a dental, dental-medical or dental-technical handpiece, which has an electric motor for driving a tool held by a tool receiver of the handpiece, in particular a dental drill.

2. Related Technology

Dental or dental-medical handpieces normally include an instrument section for receiving a rotating dental tool, for example a drill, a drive motor for driving the dental tool, and a hose section with a media delivery hose for delivering certain supply media for the operation of the handpiece. Hereunder there fall for example current for operating an electric motor and/or a light source, but also cooling media such as air and water.

FIGS. 11 and 12 show handpieces in accordance with the state of the art which are configured in different manners. As FIG. 11 shows, an instrument section 101, a drive motor 103 and a hose section 102 with a media delivery hose 104 can be configured as individual components which can then be coupled directly behind one another by plugging on. This construction thus has three coupling points between the instrument section 101 and the hose section 102, and respectively between the drive motor 103 and the two sections 101 and 102. Such a construction for a handpiece is known for example from DE 28 34 099 C2 or EP 0 012 871 B1.

A form of construction alternative to this for a dental or dental-medical handpiece is illustrated in FIG. 12. A drive motor 203 is now a so-called motor cartridge which is kept in a cavity formed by an instrument section 201 and a hose section 202. The instrument section has for this purpose a housing overlapping a drive motor 203 with integrated supply lines for receiving the supply media delivered by the media delivery hose, wherein the housing and the supply lines of the instrument section 201 are led up to the hose section 202.

These two known forms of construction are problematic in multiple regards. Thus for example, due to the great structural length, dictated by the form of construction, and the relatively great weight of the dental handpiece, handling is made more difficult since the center of gravity is shifted towards the hose side. However, delicate and easy handling is required precisely for dental work. Further, the many coupling points or separation points between the components of the handpiece are critical with regard to hygiene requirements.

To avoid these issues, correspondingly a new concept has been proposed in EP 0 888 091 A1, in which both the handpiece and the motor are divided into two components. A first section of the handpiece thereby serves for receiving a dental tool and is releasably couplable with a second section to which a medium supply line for the supply of certain supply media for operation of the tool can be connected. In turn the drive motor is divided into a rotating region and a static region with a stator winding, wherein both parts are so respectively arranged in the two sections of the handpiece that through assembly of the first and second handpiece sections the static region of the drive motor with the stator winding is pushed over the rotating region of the drive motor. In this way on the one hand the structural length of the handpiece and on the other hand the number of interfaces can be reduced in comparison with the concepts illustrated in FIGS. 11 and 12.

GENERAL DESCRIPTION OF THE INVENTION

The present invention is based on the object of indicating a further improved concept for a dental, dental-medical or dental-technical handpiece, which in comparison with the known configurations can be kept even more compact and makes possible a further improved handling.

The object is achieved by a dental, dental-medical or dental-technical handpiece dental, dental-medical or dental-technical handpiece (1), having an elongate grip sleeve (2)

a) there being arranged at the rearward end of the grip sleeve coupling elements (4) for the connection of the handpiece (1) to a supply hose (31) to be connected with a dental supply arrangement, and b) there being arranged at the forward end of the grip sleeve a head section (3) with a tool receiver (5) for mounting a tool to be put into rotation, wherein the handpiece (1) further has an electric motor (10) for driving a tool held by the tool receiver (5), characterized in that, the electric motor (10) is completely integrated into the grip sleeve (2) such that it forms a unit with the grip sleeve (2).

The solution in accordance with the invention is based on the use of new electric motors which in comparison with earlier configurations are configured considerably more compactly and nevertheless are effective. It is proposed now to use such an electric motor for the operation of a dental or dental-medical handpiece, whereby motor is preferably a so-called collectorless or brushless motor with a permanent magnet rotor, and to integrate this completely into an elongate grip sleeve of the handpiece.

In accordance with the present invention there is thus proposed a dental, dental-medical or dental-technical handpiece which has an elongate grip sleeve, at the rearward end of which there are provided coupling elements for the connection of the handpiece to a supply hose to be connected with a dental supply facility, and at the forward end of which there is arranged a head section having a tool receiver for mounting a tool which is to be set into rotation. The handpiece has further an electric motor for driving a tool held by the tool receiver, wherein in accordance with the invention it is provided that the electric motor is integrated completely into the grip sleeve so that it forms a unit with this. The grip sleeve is here constituted in one piece in accordance with a particularly preferred embodiment or consists of a plurality of parts which are not separable for a user of the handpiece.

The advantages arising with the solution in accordance with the invention are extremely various. Thus, firstly there is achieved a shortened structural form through the complete integration of the electric motor into the grip sleeve of the handpiece, what leads to improved ergonomics. This can be explained by a reduced weight for the handpiece as well as smaller effective lever arms. A further advantage consists in that motor speeds in a very broad range of 10,000-300,000 rpm, preferably from 75,000-250,000 rpm, can be used, for which reason there can be used fewer and more simply configured transmission elements for transmission of the rotation movement. Overall, the number of mechanical components for the transmission of movement can be reduced considerably with the solution in accordance with the invention, which results in better controllable production, low production costs as well as improved maintenance friendliness. The hygiene of the handpiece is also improved with the solution in accordance with the invention since the interfaces or couplings provided or required in the state of the art between a motor part and further handpiece components are omitted. Finally, the operating noise of the handpiece is also reduced, since the masses moved in operation are considerably less than in the handpieces known from the state of the art.

In accordance with an advantageous development of the present invention the grip sleeve is angled, whereby it can then be provided that the tool receiver is connected with the motor via a shaft which extends through the forward region of the grip sleeve. This shaft can be coupled with the shaft of the motor via a knee transmission; in turn at the forward end a coupling with the tool receiver in the head section of the handpiece can be effected via a head transmission. This head transmission preferably causes a reversal of direction of rotation, wherein the motor then is controlled for counter-clockwise rotation. Here, it can further be provided that one of the transmissions effects a translation which may lie in the region between 2:1 and 1:2.

The motor has preferably a max. speed of rotation of 250, 000 rpm. The head section can be arranged, with regard to the forward end of the handpiece, at an angle of about 100°, through which handling is further improved.

Other developments of the invention concern in particular the configuration and mounting of the motor within the handpiece in accordance with the invention. Here it is provided—as already mentioned—in accordance with an advantageous development of the invention, that a collectorless or brushless dc motor (BLDC-Motor) having at least one rotating permanent magnets is put to use, which distinguishes itself due to its high efficiency. In order to be able to effectively protect the sensitive components of this motor during the regularly needed sterilizing process required with such handpieces, there are now provided particular measures which are the subject of further dependent claims.

Thus, firstly, the permanent magnet or magnets of the rotor can be provided with a special coating which protects these from corrosion. A protection of the sensitive stator windings and the stator laminations can, in contrast, be achieved in that the stator is surrounded by a plastic encasing or plastic overmolding capable of being sterilized. The stator in particular is entirely cast into plastic, whereby this plastic also then forms the motor housing. In the end, there is provided through this a sheathing for the complete motor unit by which this is protected effectively against the high temperatures and atmospheric humidity during the sterilizing process. A high performance plastic which is sold under the brand name PEEK has turned out to be particularly preferred material for the realization of the plastic sheathing. This material also distinguishes itself due to its good material characteristics, especially also at high temperatures such as arise in sterilization, and is further hydrolysis resistant.

The use of the plastic housing then leads however to the issue that the plastic has a different thermal expansion coefficient than the surrounding material of the handpiece sleeve. To avoid or reduce the stresses arising hereby between handpiece sleeve and plastic housing it is provided in accordance with a particularly advantageous development of the invention, that the motor is mounted in a special manner within the handpiece sleeve. In particular no fixed screwing together of the motor with the sleeve is provided but instead a sprung mounting is provided. Through this a certain flexibility is created, whereby however through the spring force it is ensured that the motor is in principle urged with a substantially uniform force against a stop within the grip sleeve. The spring used for this thus compensates for corresponding different expansions of the grip sleeve and the motor housing. This particular mounting leads on the one hand to damage to the motor being avoided, on the other hand it is ensured that the motor is arranged permanently in the same manner within the grip sleeve, which is of advantage to the extent that through this a very exact coupling with further power transmission elements of the drive is ensured.

Dental or dental-medical handpieces normally also have an illumination arrangement via which the region to be worked in the mouth of a patient is illuminated during the use of the handpiece. Such a measure can be provided also with the handpiece in accordance with the invention, whereby for this purpose preferably a light guide is used which extends from the coupling elements of the handpiece up to a light exit point in the forward end region. This light guide is configured in particular in one piece and extends thus continuously to the light exit point, whereby it is taken past the motor, which is arranged preferably slightly eccentrically within the grip sleeve. Further, media lines can extend through the handpiece which serve for the supply of air and/or water. Here, appropriate filter facilities can also be arranged within the handpiece.

BRIEF DESCRIPTION OF THE DRAWINGS

The invention will be explained in more detail with reference to the accompanying drawings. There is shown.

DETAILED DESCRIPTION

Figure 1:
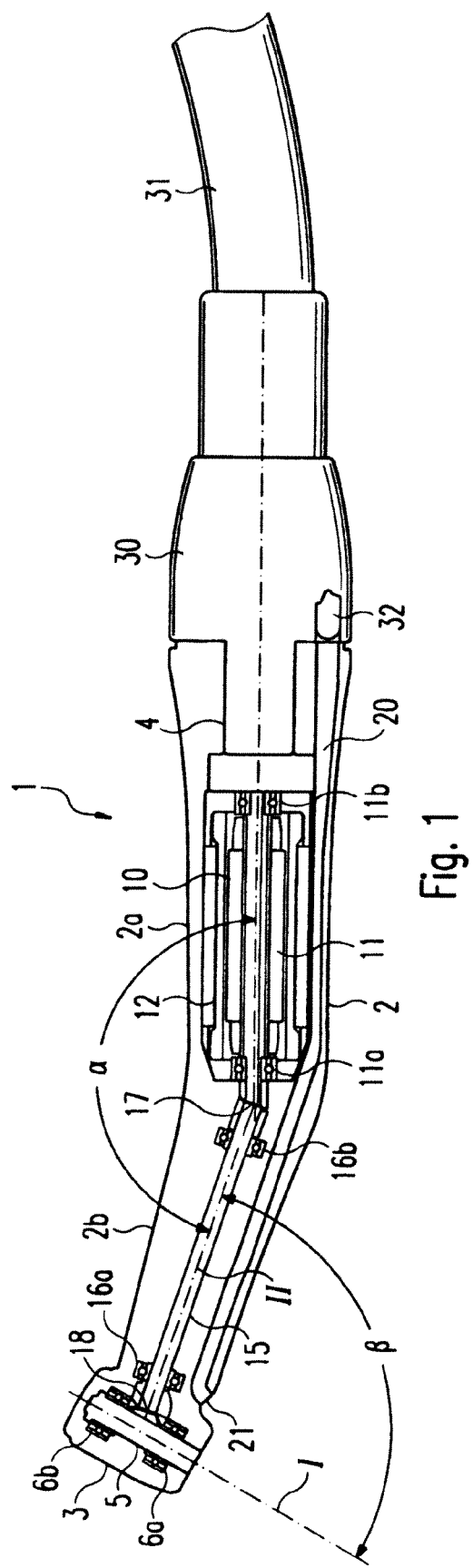
FIG. 1 schematically an embodiment of the present invention in form of a dental angled handpiece configured in accordance with the invention.

The dental or dental-medical handpiece in accordance with the invention which is illustrated schematically in FIG. 1 and provided overall with the reference sign 1 has as main element an elongate grip sleeve 2. In the illustrated embodiment the handpiece 1 is constituted as a so-called angled handpiece. The grip sleeve 2, constituted in one piece, has a rearward region 2b and a forward region 2a which include with one another an angle α of about 155° to 170°, preferably of 162°. The handling of the handpiece 1 within the mouth of a patient is simplified by this configuration.

The head section of the handpiece 1 is located at the forward end of the grip sleeve 2, which head section has a tool receiver 5 mounted rotatably by means of two bearings 6a, 6b. This tool receiver 5 has a chuck, not illustrated in more detail, for the selective mounting of a dental treatment tool which, set in rotation, is put to use for material removing working. The tool receiver 5 of the head section 3 is provided in particular for the rotatable mounting of dental drills. To further improve the ergonomic qualities of the handpiece 1, the head section 3 is further so configured in accordance with the invention such that the longitudinal axis I of the tool receiver 5 includes with the axis II of the forward end region 2b of the grip sleeve an angle β of about 100°. In comparison with classical configurations of angled handpieces, in which the drill is directed at a right angle to the grip sleeve, this preferred form leads to a further improved handling.

At the rearward end the grip sleeve 2 is connected with the connecting part 30 of a supply hose 31 which in particular leads to a supply facility (not illustrated) of a dental treatment station. Via this supply hose 31 the handpiece 1 is provided with the required media for operation, in particular current. This current is used—as explained in more detail below—for the operation of the motor and could further be used also to provide illumination. Furthermore, however, also additional treatment media such as air and/or water can be provided, which can be used either individually or also as an air/water mixture which could be used for example for cleaning the surface to be worked. The media lines extending in addition through the handpiece 1 in this case are in the present case not illustrated in more detail, for reasons of simplicity. Their arrangement in the handpiece 1 will be is explained in more detail below. If such lines are present, also corresponding media filters can further be arranged in the handpiece 1.

The connection of the handpiece 1 is then effected via a coupling element 4 situated in the rearward end of the grip sleeve 2, via which a connection with the hose connection part 30 is effected. The connection, preferably configured as a bayonet coupling, can for example be so configured that the handpiece 1 is rotatable freely. As will be explained in more detail below, the coupling in the illustrated embodiment is however so configured that there is a fixed orientation between handpiece 1 and hose connection part 30.

Dental handpieces can be in principle be configured with different drives. Classically, air or turbine drives or electrical drives are, for example, put to use. A turbine thereby distinguishes itself due to its compact manner of construction, on the other hand the operational reliability is lesser in comparison with an electric motor. Further, in comparison with an electric motor the possibility of controlling the power to be transmitted is available only to a restricted extent.

Electric motors have, however, to date the disadvantage that by their use the structure of the handpiece was enlarged. In the present case there is now however put to use as electric motor a micromotor which is mounted completely within the grip sleeve 2 of the handpiece 1. The motor, provided overall with the reference sign 10, has on the one hand a stator 12 mounted in the handpiece sleeve fixedly, i.e. non-rotatably, and on the other hand a rotor 11 mounted rotatably with respect to this stator 12 with the aid of two bearings 11a and 11b. The exact configuration of the motor 10 will be explained in more detail later. It is of particular importance for the time being that the dimensions of the motor 10 are kept very compact, so that this is integrated into the grip sleeve 2 completely. Here, it has to be taken into account in particular that the grip sleeve 2 is configured in one piece or is of a plurality of parts which for the user are connected inseparably with one another, and correspondingly there arise no connection interfaces such as arise with the known configurations in accordance with the state of the art. The electric motor 10 is correspondingly constituted for a permanent mounting within the handpiece sleeve 2 and forms a unit with this, for which reason it is also sterilizable, to make possible a regular cleaning and sterilization of the handpiece 1 overall.

The rotation movement produced by the motor 10 is transferred to the tool receiver 5 by means of a shaft 15, which extends through the forward grip sleeve region 2b. This shaft 15, which in turn is mounted rotatably by means of two roller bearings 16a, 16b, is for this purpose coupled at its rearward end via a knee transmission 17 with the rotor 11 of the electric motor 10; at the forward end a coupling is effected between shaft 15 and tool receiver 5 by means of a head transmission 18. The head transmission 18 can here in particular bring about a reversal of direction of rotation, whereby the electric motor 10 is then controlled preferably for counter-clockwise rotation, to bring about the desired rotation of a drill held in the tool receiver 5. Seen overall the handpiece in accordance with the invention thus has merely three rotatably mounted axes or shafts (the motor rotor 11, the intermediate shaft 15 and the rotatable tool receiver 5 with the integrated chucking system), in order to bring the drill or in general the tool into rotation by means of the voltage applied to the handpiece. This represents the ideal case whereby however—so far as necessary—also intermediate transmission stages could be put too use. In turn this would lead, however, to greater requirements for space, for which reason the illustrated embodiment is particularly preferred. Further, theoretically, a planetary gear train also could be used for the transmission of rotational speed (then with more axes of rotation).

Advantages of this particular configuration lie in that a very direct power transmission from the motor 10 to the tool receiver 3 is provided. The number of required mechanical components for motion transmission is clearly reduced in comparison with previous solutions. In turn this has the consequence that the production of the handpiece 1 can be simplified and made more economical and further also the handpiece 1 is overall repair friendlier. In this connection, it has to be taken into account that in the dental industry for the working of tooth hard substance speeds of rotation for the drill are needed in the region between 120,000 rpm and 300,000 rpm. Angled pieces which are driven mechanically by a motor via transmission elements work to date predominantly in the region of final speeds of rotation of 200,000 rpm, which is made possible in that the speed of a classical drive motor of approximately 40,000 rpm is translated by means of several transmission elements by the factor 5 to the desired 200,000 rpm. Also translations by the factors 3, 4 or 6 are occasionally in use. The transmission elements required for such a high translation consist, however, of many components which due to the high rotational speeds must be produced with the highest precision, to keep undesired surface oscillations and acoustic noise emissions as small as possible. The required precision and the number of components bring about high costs.

The, in contrast, direct power transmission present with the handpiece 1 in accordance with the invention, and the use of very high speed of rotation motors, now makes possible the use of transmissions in the case of which the speed of rotation translation lies merely in the region between 0.5 and 2, whereby despite everything the most varied ranges of speed of rotation and power ranges are available. Here it can in particular be provided that the electric motor 10 works at speeds of rotation in the region of 10,000 to 300,000 rpm, preferably of 75,000 to 250,000 rpm or at maximum up to 250,000 rpm. The knee transmission 17 and/or the head transmission 18 can then—so far as desired—have corresponding translations in the region between 1:2 and 2:1. In the end, there can thus be achieved with this, without problem, final speeds for the drill in a preferred region of 150,00 to 250,000 rpm or even up to 300,000 rpm, whereby use also in the lower motor speed range would also however be conceivable. In this case it has to be ensured that the motor 10 provides a sufficient torque.

Further, the more direct power transmission with the handpiece 1 in accordance with the invention leads, due to the less complex transmission gearings, also to a greater smoothness of running. Here it has to be said that in dental technology speeds above 80,000 rpm normally lead with regard to noise and vibration to considerable problems, which in particular is then the case if the rotational speed transmission takes place by means of a releasable coupling between a separate motor part and the angled piece. These difficulties obviously do not arise with the solution in accordance with the present invention, which can be explained in particular in that the transfer of the rotation movement is effected in each case by gear wheel pairings which cannot be separated by the user. The particularly preferred arrangement of the head section 3 at an angle of about 100° with respect to the forward end region 2b of the grip sleeve 2 can further be effected without an additional mechanical reversal of the direction of rotation. Finally, the hygiene of the handpiece 1 is improved since the use of various couplings can be omitted.

Through the complete integration of the micromotor 10 into the grip sleeve 2 the advantage is further obtained that the handpiece 1 can still be kept very compact and has a handiness which is comparable with that of a turbine handpiece. Thus the forward grip sleeve region 2b can be realized with a diameter of merely about 12 to 18 mm. The size of the head section 3 also can be further reduced in comparison with known solutions. Through this a very precise drill guiding is made possible, which in the end leads to more exact working. The use of the electric motor further also makes it possible to set the direction of rotation by a corresponding setting of the motor 10. In particular in the grinding of tooth replacements or similar elements advantages are hereby achieved since a clockwise or counter-clockwise running can be set.

To improve further the possibilities for use of the handpiece 1, the availability of an illumination can further be provided. For this purpose, a light guide 20 extends longitudinally through the grip sleeve 2, which light guide opens with its forward end in a light exit opening 21. The forward end of the light guide 20 is thereby so directed that the light is approximately directed towards the forward end region of a tool held in the tool receiver 5.

The light coupled into the light guide 20 originates from a lamp 32 which is mounted in the hose connection part 30. Correspondingly there is preferably provided a fixed orientation between handpiece 1 and hose connection part 30 such that the light of the lamp 32 can be coupled in an effective manner into the end face of the light guide 20 directed in an aligned manner. In this way an efficient illumination of the region to be worked is made possible.

Figure 2:
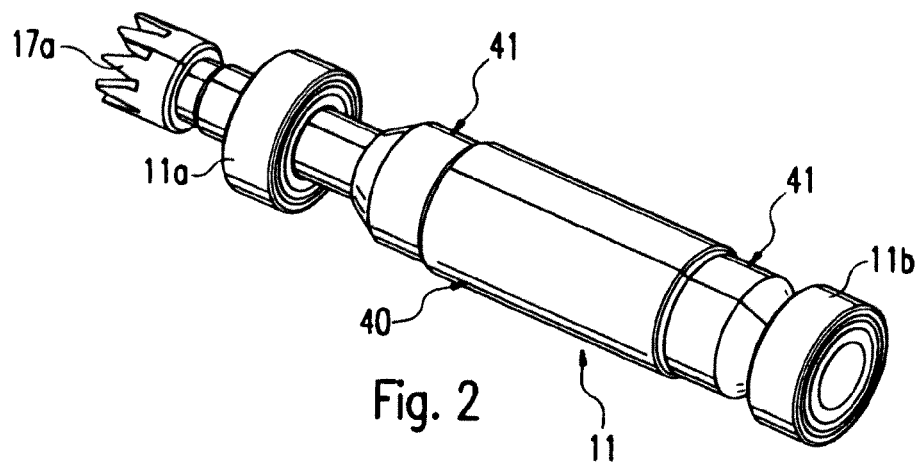
FIG. 2 a representation of the rotor of an electric motor arranged in a handpiece in accordance with the invention.
Figure 3:
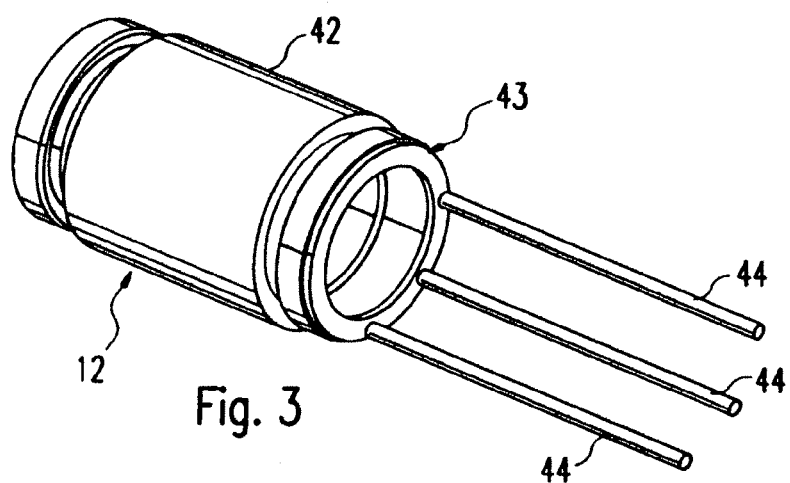
FIG. 3 the configuration of the stator of the electric motor.
Figure 4:
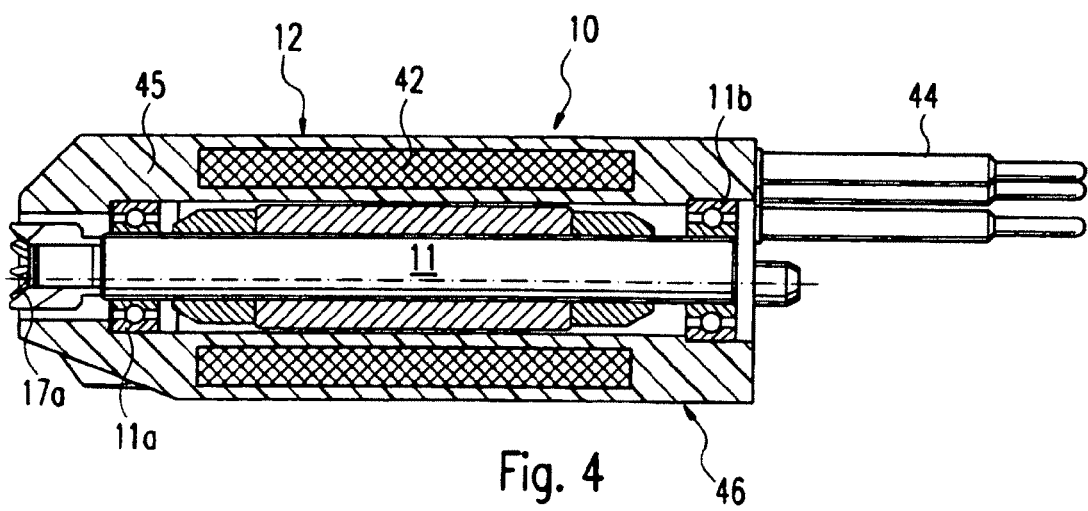
FIG. 4 a sectional illustration of the electric motor.

The integration of the electric motor 10 into the grip sleeve 2 of the handpiece 1, which represents an significant point of the present invention, is also in particular supported by a special configuration of the motor 10, which will be described in more detail below with reference to FIGS. 2 to 4. To this end, FIG. 2 shows to an enlarged scale the exterior view of the rotor 11 of the motor 10, whilst FIG. 3 shows the exterior view of the stator 12. FIG. 4 is in turn a sectional view of the motor 10 in a state in which the rotor 11 is arranged within the stator 12.

The motor 10 is preferably, as already mentioned, a collectorless or brushless dc motor with a permanent magnet rotor. Such so-called BLDC (Brushless Direct Current) motors distinguish themselves through their high efficiency which is provided in particular also by a corresponding control of the stator windings. Current supply of the stator windings adapted to the disposition or the angular position of the rotor 11, the so-called commutation, is ensured by means of corresponding control electronics which permanently detect the position of the rotor 11 and correspondingly supply the windings with current of a suitable phase. Such an approach is already known in principle for BLDC motors and correspondingly will not be explained in more detail in the following. It is merely to be remarked that the possibility exists of detecting the disposition of the rotor 11 either through the use of corresponding non-illustrated sensors or through the development of the current through the stator windings. The motor has a power of more than 10 watts, in particular a power in the region between 10 and 30 watts.

Since in accordance with the present invention the motor 10 is to remain permanently in the grip sleeve 2 of the handpiece 1, now however particular measures must be taken which make possible a cleaning or sterilization of the handpiece 1 without the components of the motor 10 thereby being damaged.

For this purpose, firstly it is provided that the permanent magnet or magnets 40 of the rotor 11 illustrated in FIG. 2, which are normally very sensitive to corrosion, are specially coated, preferably nickel-plated. Such a coating protects the surfaces of the permanent magnets 40, which are formed preferably by so-called rare earth magnets, from the hot vapors during the sterilizing process and provides that no particular sealing of the motor 10 is required. The rotor magnet or magnets 40 are thereby arranged according to the illustration in accordance with FIG. 2 between two weighting rings 41, whereby the resulting arrangement, at the forward end of which the gear wheel 17a is arranged for rotational movement transmission, is then mounted by means of two ball bearings 11a and 11b in the stator winding 12.

In turn the stator winding 12 also is constituted in a special manner, in order on the one hand to make possible a high efficiency of the motor 10 and on the other hand the desired sterilizability.

With regard to the desired high efficiency of the motor 10, firstly it has to be taken into account that a high efficiency and thus a slight heating only then can be achieved at the desired high rotational speeds if the no-load losses, which are caused by the rotating magnetic field of the rotor 11, are kept as slight as possible. These losses divide into magnetic reversal losses and eddy current losses in the stator lamination. To keep these losses as slight as possible therefore, the stator 12 is realized from a plurality of laminations 42, arranged behind one another in an axial direction, which are of a nickel-iron alloy. On the one hand, this material distinguishes itself through a relatively high so-called saturation induction and on the other hand through to a high specific electrical resistance. It is further decisive that the laminations 42 used have an extremely slight thickness preferably of merely 0.1 mm, which enables the eddy current losses to be kept extremely slight.

For the protection of this arrangement the stator laminations 42 as well as the windings 43 of the stator 12 are then embedded completely in a washable or sterilizable plastic 45, as can in particular be understood from the sectional view in FIG. 4. By this encapsulation or sheathing 45, within which the two bearings 11a and 11b are also arranged and from which merely the connections 44 for the windings 43 of the stator 12 project rearwardly outwardly, a penetration of water or dirt into the windings 43 is prevented. Further, the return path lamination of the stator 12 can in turn be protected against corrosion in special manner, for example with the aid of a corresponding coating. Especially the sensitive stator windings 43 as well as the stator laminations 42 can in this way be protected in an effective manner. As can be understood from the illustration in FIG. 4, the plastic sheathing completely encloses these sensitive components of the motor 10. This plastic sheathing therefore provides overall a protection for the motor 10 in form of a motor housing 46, since through this also the rotor 11 is enclosed to the greatest extent. Merely by means of the two bearings 11a, 11b, at the forward and rearward end of the rotor 11, could a slight component of hot steam and other media penetrate into the interior of the stator 12. The coating of the rotor magnet or magnets 40 then offers in this case however a sufficient protection during the washing or sterilization process, so that no separate particular protection, e.g. a special sealing the handpiece 1, is required.

The plastic PEEK is preferably used as material for the encapsulation or sheathing 45. This plastic, which is available both in readily flowing and in glass fibre reinforced variants, has proved to be particularly advantageous with regard to the desired sterilizability, since this material has good material characteristic values also at high temperatures and is further hydrolysis resistant.

Further, it has to be emphasized that the bearings 11a, 11b are fixedly integrated in the stator 12. The motor 10 correspondingly forms a compact physical unit. In this case the complete cooling air is passed through the air gap between rotor 11 and stator 12, wherein a part of the air can be led back on the outside over the stator, which leads to a further cooling effect. The other part of the air in turn flows over the transmission in the forward region of the handpiece 1 and exits here. A lubrication of the motor bearings 11a, 11b is also effected via the air gap. Seen overall there can thus be obtained an electric motor which is kept very compact, with an extremely high efficiency.

The idea of realizing the housing 46 of the motor 10 by means of a plastic sheathing 45 with an injected stator 12 leads, however, to a further issue which will be explained—with the solution thereof—in the following.

Figure 5:
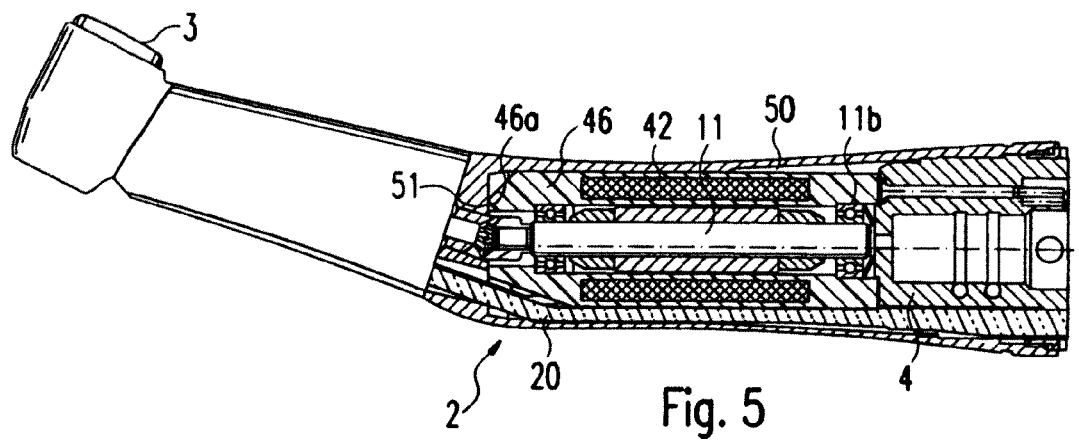
FIG. 5 the mounting of the electric motor within the handpiece sleeve.
Figure 6:
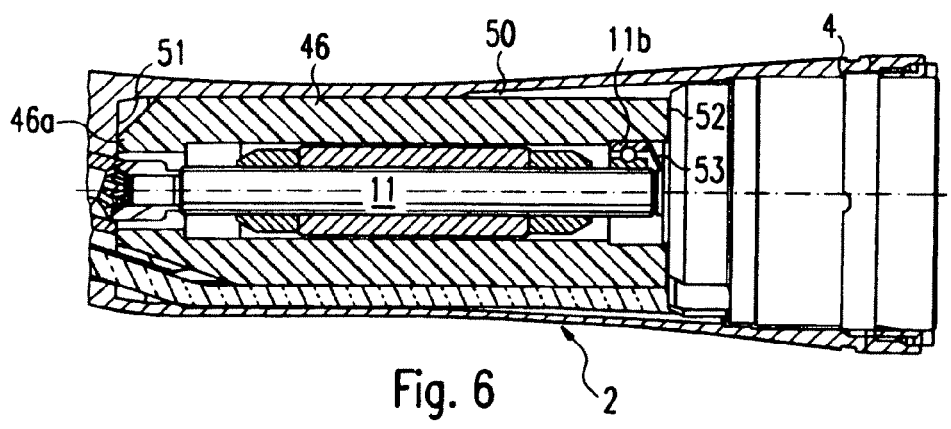
FIGS. 6 and 7 details, to an enlarged scale, of the illustration of FIG. 5.
Figure 7:
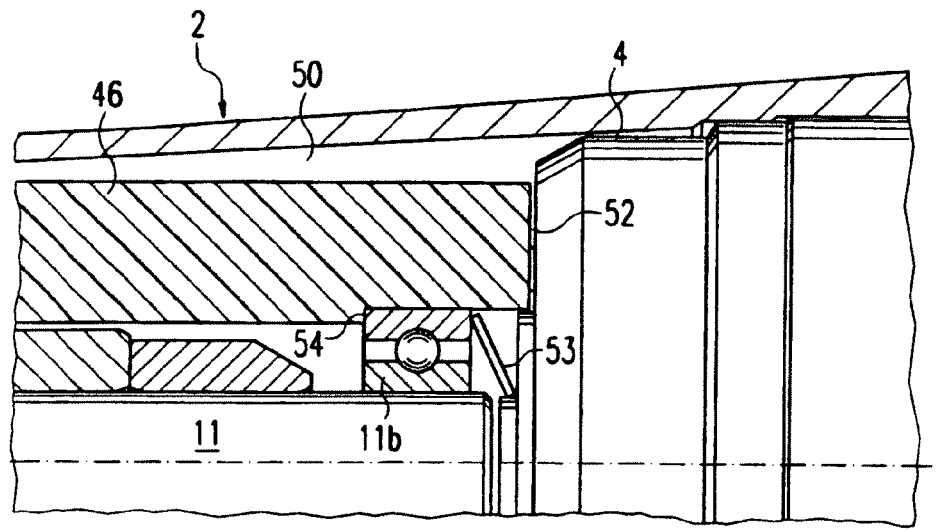

Thus the housing 46 of the motor 10 in the handpiece 1 should not stand permanently under a too great a stress since otherwise it can come to damage in particular during sterilization, due to different thermal expansions of the components. A rigid installation of the motor 10, for example through corresponding screw connection of the components, would therefore lead to difficulties because, due to the higher thermal expansion coefficient of the plastic housing 46 with respect to steel, the axial stresses would increase upon heating. Since on the other hand the motor axis mounted in the motor housing 46 or the stator 11 must be positioned very exactly due to the required high precision of the tooth engagement of the coupling element 17, a special mounting of the motor 10 in the handpiece sleeve 2 is proposed which can in particular be understood from the illustrations in FIGS. 5 to 7.

The solution of the problem described above consists in that the motor housing 46 mounted in a cavity 50 of the grip sleeve 2 bears with its forward end 46a on a fixed stop 51 within the instrument sleeve 2. At the rearward end of the motor 10 there is present, in contrast, an air gap 52 to the coupling insert 4 fixedly screwed into the instrument sleeve 2, whereby this air gap 52 can be understood in particular in the representation to an enlarged scale in FIGS. 6 and 7, in which only the rear bearing 11b is partly illustrated. At the coupling insert 4 there is in turn arranged a plate spring 53 which bears axially on the one hand on the coupling insert 4, and on the other side bears on the outer ring of the rearward ball bearing 11b of the motor axis 11. This outer ring directs the spring force of the plate spring 53 via a bond 54 into the motor housing 46 which in this way is urged against the forward stop 46a of the instrument sleeve 2.

If it now comes for example to an expansion of the housing 46 due to a warming of the motor housing 46 for example during sterilization, then the plate spring 53 is slightly compressed. The axial force that acts on the housing 46 however practically does not increase so that stresses during the sterilizing process can be reduced. The air gap 52 is thereby dimensioned such that it can take up the expansion occurring without the motor housing 46 standing on the coupling insert 4. In combination with the measures for the configuration of the motor 10 described above the result is provided that the motor 10 is protected in extremely effective manner on the one hand against external influences and on the other hand is reliably permanently mounted within the handpiece sleeve 2. Thereby, the mounting is in particular such that the correct arrangement of the motor axis, in particular of the coupling element 17b, with respect to the gear wheel of the forward drive shaft 15 is permanently ensured.

Figure 8:
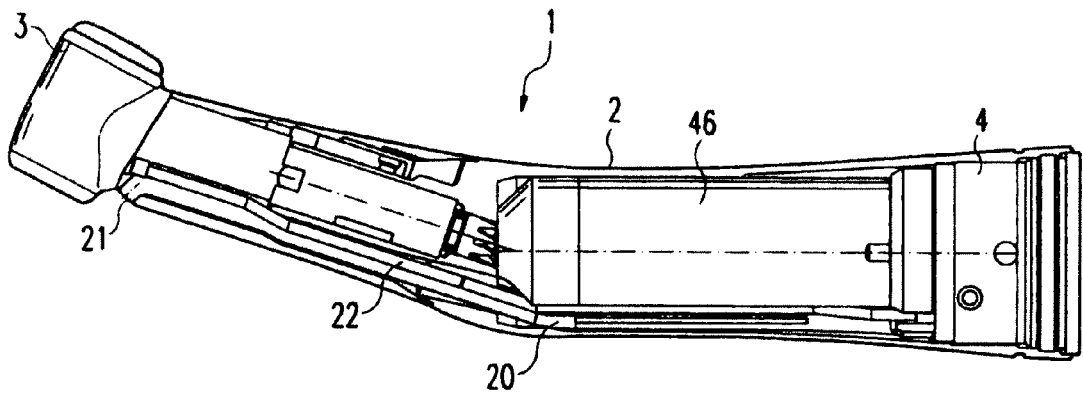
FIGS. 8 and 9 a part section of the handpiece for clarification of the course of the media lines and a light guide.
Figure 9:
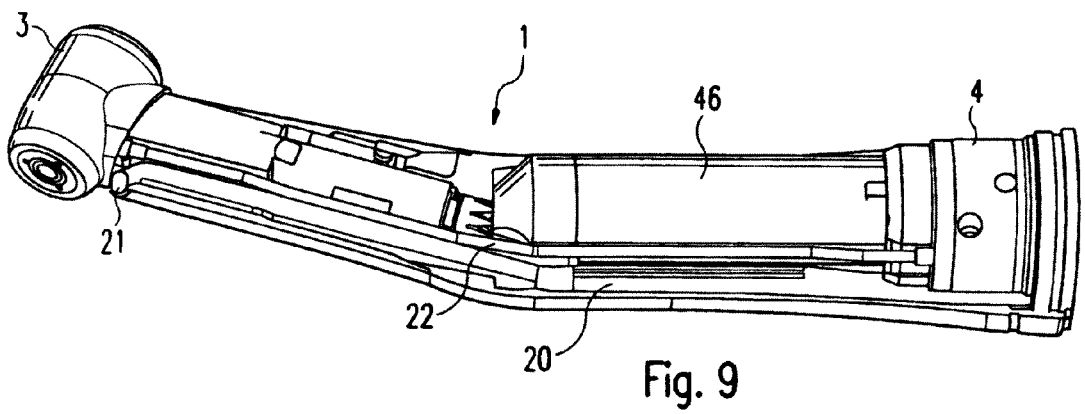
Figure 10:
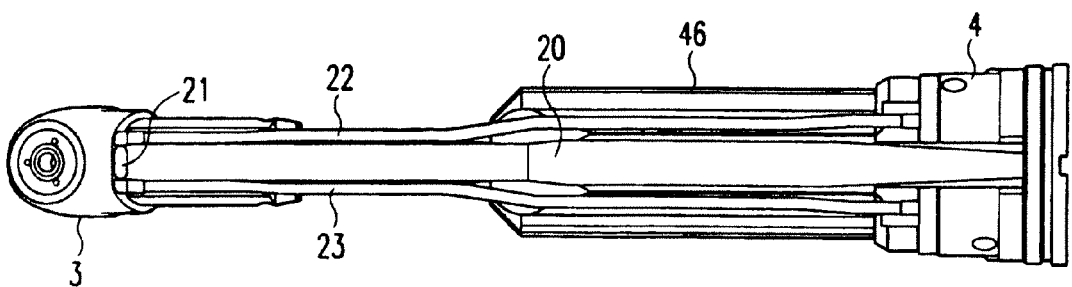
FIG. 10 a further view of the media lines running along the handpiece.
Figure 11:
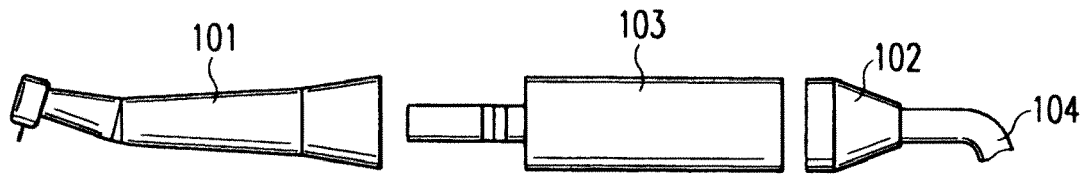
FIGS. 11 and 12 concepts for dental handpieces known from the state of the art.
Figure 12:
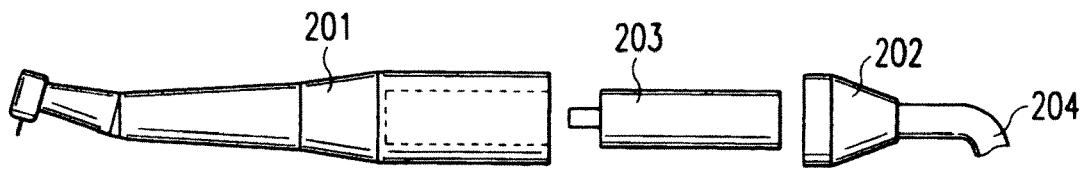

As already mentioned above, the motor 10 configured in accordance with the invention also distinguishes itself in particular due to its compact arrangement within the handpiece sleeve 2. This makes it possible to pass additional lines through the sleeve, to make available cleaning or cooling mediums required during treatment. In accordance with the illustrations in FIGS. 8 to 10 it is provided in particular that the motor 10 is arranged slightly eccentrically within the sleeve and corresponding media lines 22, 23 are firstly led past the underside of the motor housing 46 and then led to the handpiece head 3. These media lines 22, 23 serve in particular for the supply of air and water, whereby also the possibility is provided of issuing both media at the same time in the form of a spray. Between the two media lines there is further carried the above-mentioned light guide rod 20 which extends from the coupling part 4 up to the forward light exit 21 and makes possible an illumination of the region being worked. The mentioned eccentric arrangement of the motor 10 is thus in particular of advantage if a plurality of lines run in the handpiece sleeve 2. In case, however, that a delivery of light and spray media is not provided and no accompanying lines or light guides correspondingly run in the handpiece, the motor 10 could of course also be arranged centrally within the sleeve 2.

In the end, there is thus provided a handpiece which has clear advantages over previous handpieces having electric motors with regard to its dimensions, its handling and its operational characteristics. Through this, further possible applications are provided for the handpiece since the high speed drive can be used also for example for applications in the ENT field, in microsurgery or in minimally invasive treatments.

The invention claimed is:
1. A sterilizable dental handpiece comprising:
an elongate tubular member having a proximal end having a first coupling member adapted to connect to a second coupling member supplying electrical power and fluid under pressure to the handpiece, and a distal end having a tool receiver for detachably holding a dental tool in the handpiece;
a brushless electric motor in the tubular member toward the proximal end comprising a stator having electric windings, and a rotor comprising a central axial shaft and permanent magnets carried on the shaft, the stator being positioned in an annular chamber in the tubular member and being sealed to protect the stator windings against exposure to moisture and contaminants;
an electrical lead extending from the first coupling member at the proximal end of the tubular member into the chamber to conduct electrical power to the stator windings;
bearings mounting the rotor for rotation within and relative to the stator and securing the rotor against axial movement within the tubular member;
a spring member disposed between the second coupling member and a bearing mounting the rotor; and
a drive transmission toward the distal end of the tubular member mounted for rotation within the tubular member and connecting an end of the rotor to the tool receiver for rotating the tool receiver when the motor is activated;
wherein the motor and transmission are fixedly mounted within the handpiece with the handpiece presenting an end for connection to both sources of supply of electrical power and of fluid to the handpiece for reducing the length and weight of the handpiece for ease of use.

2. The sterilizable dental handpiece of claim 1, wherein the motor comprises a rotating region and a static region receiving the stator windings, the static region of the motor being moved over and surrounding the rotating region of the motor when the motor is inserted into the internal chamber for enabling the motor to integrate completely into the internal chamber of the handpiece.

3. The dental handpiece of claim 1, wherein the motor comprises a rotating region and a static region receiving the stator windings, wherein the stator is cast into a sheathing.

4. The dental handpiece of claim 3, wherein the stator sheathing forms the motor housing.

5. The dental handpiece of claim 4, wherein the stator sheathing is formed of a material capable of withstanding sterilization temperature and humidity.

6. The dental handpiece of claim 1, wherein the motor is completely integrated into the grip sleeve such that the motor forms a unit with the grip sleeve.

7. The dental handpiece of claim 1, wherein the tool receiver is configured for mounting a tool that is to be set into rotation.

8. The dental handpiece of claim 1, wherein the tool receiver is connected to the motor via a shaft that extends through the forward region of the grip sleeve.

9. The dental handpiece of claim 8, wherein the shaft is coupled with a motor shaft via a knee transmission.

10. The dental handpiece of claim 9, wherein the shaft is coupled with the tool receiver via a head transmission at a forward end of the shaft.

11. The dental handpiece of claim 1, wherein a rotor of the motor includes a corrosion resistant coating.

12. The dental handpiece of claim 1, wherein the tubular member comprises a sleeve at an outer surface thereof, and the motor is spring mounted within the sleeve and is biased against a forward stop formed in the sleeve.

13. The dental handpiece of claim 1, further comprising at least one coupling element and one light guide, the light guide extending from the coupling element to a light exit point.

14. The dental handpiece of claim 1, further comprising a supply hose for providing fluid media required for operating the handpiece.

15. The dental handpiece of claim 1, wherein the motor is a brushless motor.

* * * * *